United States Patent [19]

Illig et al.

[11] Patent Number: 5,310,537
[45] Date of Patent: May 10, 1994

[54] COMPOSITIONS OF IODOANILINE DERIVATIVES FOR VISUALIZATION OF THE GASTROINTESTINAL TRACT

[75] Inventors: Carl R. Illig, Phoenixville; Thomas J. Caulfield, Audubon, both of Pa.

[73] Assignee: Sterling Winthrop Inc., Malvern, Pa.

[21] Appl. No.: 24,555

[22] Filed: Mar. 1, 1993

[51] Int. Cl.$^5$ ................... C07C 211/45; G01N 21/00
[52] U.S. Cl. ........................................ 424/5; 564/218; 564/442
[58] Field of Search ................. 564/218, 442; 424/5

[56] References Cited

U.S. PATENT DOCUMENTS

| | | | |
|---|---|---|---|
| 2,820,814 | 1/1958 | Ginsberg | 260/471 |
| 3,360,436 | 12/1967 | Felder et al. | 167/95 |
| 3,666,803 | 5/1972 | Holtermann | 424/5 |
| 3,733,397 | 5/1973 | Bjork et al. | 424/5 |
| 3,795,698 | 3/1974 | Soulal et al. | 260/471 R |

OTHER PUBLICATIONS

Tomaschewski, J. Prakt. Chem., vol. 33(1966) 168,176.
Gregory et al, Chemical Abstracts, vol 92(1980) 24221y.
Galliani et al, Chemical Abstracts, vol. 86(1977) 154932t.
Waring, Chemical Abstracts, vol. 57(1962) 13674d.
Wade et al, J. Chem. Soc. C(1968) pp. 1338–1339.
Ding et al, Chemical Abstracts, vol. 111(1989) 38939m.
Watanabe et al, Chemical Abstracts, vol. 104(1986) 43171q.
Cowan et al, Chemical Abstracts, vol. 97(1982) 140355x.
Starkun, Chemical Abstracts, vol. 94(1981) 191421m.
Bowman et al, Chemical Abstracts, vol. 116(1992) 128832d.
Curran et al, Chemical Abstracts, vol. 115(1991) 114108q.
Amaike, Chemical Abstracts, vol. 113(1990) 217816g.
Okada et al, Chemical Abstracts, vol. 112(1990) 178346m.

*Primary Examiner*—Richard L. Raymond
*Attorney, Agent, or Firm*—Arthur Rosenstein; Imre Balogh

[57] ABSTRACT

Disclosed are contrast agents of the formula

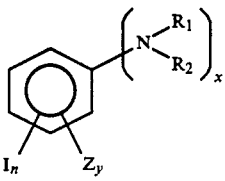

contained in aqueous compositions and methods for their use in diagnostic radiology of the gastrointestinal tract wherein Z=H, halo, $C_1$–$C_{20}$ alkyl, cycloalkyl, lower alkoxy, cyano, where the alkyl and cycloalkyl groups can be substituted with halogen or halo-lower-alkyl groups;

$R_1$ and $R_2$ are independently H, $C_1$–$C_{25}$ alkyl, cycloalkyl, acetyl or halo-lower-alkyl, wherein said $C_1$–$C_{25}$ alkyl, cycloalkyl, acetyl and halo-lower-alkyl are optionally substituted with fluoro-lower-alkyl, aryl, lower-alkoxy, hydroxy, carboxy, lower-alkoxy carbonyl or lower-alkoxy-carbonyloxy, n is 1–4;
y is 1–4; and
x is 1 or 2.

28 Claims, No Drawings

COMPOSITIONS OF IODOANILINE DERIVATIVES FOR VISUALIZATION OF THE GASTROINTESTINAL TRACT

BACKGROUND OF THE INVENTION

1. Field of the Invention

This invention relates to aqueous compositions containing the contrast agent iodoaniline derivatives and methods for their use in diagnostic radiology of the gastrointestinal tract.

2. Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946.) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor X-ray images. In the colon, when administered as an enema, it flocculates and forms irregular clumps with fecal matter.

Iodinated organic compounds have also been used as GI contrast agents since the iodine atom is an effective X-ray absorber. They have the most versatility and are utilized in the widest variety of procedures. They are very absorptive of X-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 3,574,718; 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

We have found that compounds having these and other desirable characteristics in the GI tract should preferably have the following properties for inclusion in a suitable pharmaceutically acceptable vehicle for oral or rectal administration:

a partition coefficient, i.e. the ratio of hydrophobicity to hydrophilicity of about 10 or higher;

a melting point of less than about 80° C.; and a molecular weight of at least about 200.

We have found that certain compounds hereinafter described possess these desirable properties when used in aqueous oral and rectal formulations for examination of the GI tract utilizing X-rays and CT scans.

SUMMARY OF THE INVENTION

In accordance with the invention, there is provided an x-ray contrast composition comprising solid particles of a contrast agent having:

a partition coefficient of about 10 or higher, and preferably, from about $10^2$ to about $10^8$;

a melting point of less than 80° C., and preferably less than 60° C.; and a molecular weight of at least 200, and preferably from about 200 to about 2,000; and a pharmaceutically acceptable aqueous carrier therefor.

In accordance with the present invention, there is also provided an x-ray contrast composition comprising a liquid x-ray contrast agent having:

a partition coefficient of about 10 or higher, and preferably, from about $10^2$ to about $10^8$;

a molecular weight of at least 200, and preferably from about 200 to about 2,000; and a pharmaceutically acceptable aqueous carrier therefor.

In accordance with the invention there is further provided a method for x-ray diagnostic imaging of the GI tract which comprises orally or rectally administering to the patient an effective contrast producing amount of one of the above-described x-ray contrast compositions.

The composition for radiological examination of the GI tract comprises a compound of the formula:

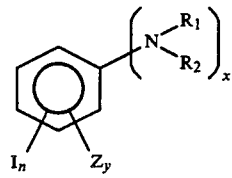

or a pharmaceutically acceptable salt thereof
wherein
Z=H, halo, $C_1$–$C_{20}$ alkyl, cycloalkyl, lower alkoxy, cyano, where the alkyl and cycloalkyl groups can be substituted with halogen or halo-lower-alkyl groups:

$R_1$ and $R_2$ are independently H, $C_1$–$C_{25}$ alkyl, cycloalkyl, acetyl or halo-lower-alkyl, wherein said $C_1$–$C_{25}$ alkyl, cycloalkyl, acetyl and halo-lower-alkyl are optionally substituted with fluoro-lower-alkyl, aryl, lower-alkoxy, hydroxy, carboxy, lower-alkoxy carbonyl or lower-alkoxy-carbonyloxy;

n is 1–4;

y is 1-4; and x is 1 or 2.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or more iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100 μ provides for good distribution and coating in the GI tract. As used herein, particle size refers to a number average particle size as measured by conventional techniques, such as sedimentation field flow fractionation and disk centrifugation. An effective average particle size of less than about 100 μ means that at least about 90% of the particles have a weight average particle size of less than about 100 μ as measured by art recognized techniques.

A method for diagnostic imaging of the GI tract for use in medical procedures in accordance with this invention comprises orally or rectally administering to the mammalian patient in need of an x-ray examination, an effective contrast producing amount of a composition of the present invention. After administration at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the procedures known in the art using commercially available starting materials, intermediates and reagents. Starting materials, reagents and solvents can be obtained from chemical suppliers such as Aldrich, Baker and Eastman Chemical Companies, or they may be prepared by techniques known in the art.

The following examples will further illustrate the compounds used in the present invention.

EXAMPLE 1

N-acetyl-N-2'-octyl-4-iodoaniline

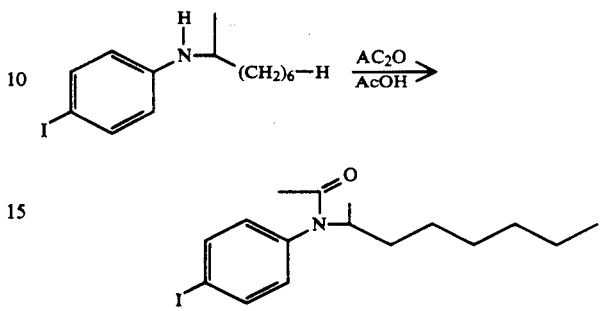

A flask containing N-(4'-iodophenyl)-2-amino octane (1.50 g, 4.5 mmol) was charged with acetic acid (15 ml) and acetic anhydride (15 ml). The reaction flask was immersed in an oil bath which was warmed to 70° C. over a period of 0.5 hr. After stirring for 19 hrs, the reaction was allowed to cool, diluted with ether (200 ml), washed with water (2×50 ml), saturated aqueous sodium bicarbonate (4×50 ml), water (2×50 ml) and brine (50 ml), dried ($Na_2SO_4$), filtered, and evaporated in vacuo. Flash column chromatography (silica, 1:4; EtOAc:hexanes) provided N-acetyl-N-2'-octyl-4-iodoaniline (1.48 g, 70%) as a white solid. Mp 60°-62° C.

Title Compound: $^1H$ (300 MHz) and $^{13}C$ (75 MHz) NMR spectra were consistent with the desired structure. FAB/MS MH+ 374. Calculated for $C_{16}H_{24}NIO$: C, 51.48; H, 6.48; N, 3.75; I, 34.00. Found: C, 51.68, H, 6.46; N, 3.67; I, 33.87.

EXAMPLE 2

N-(4'-iodophenyl)-2-amino octane

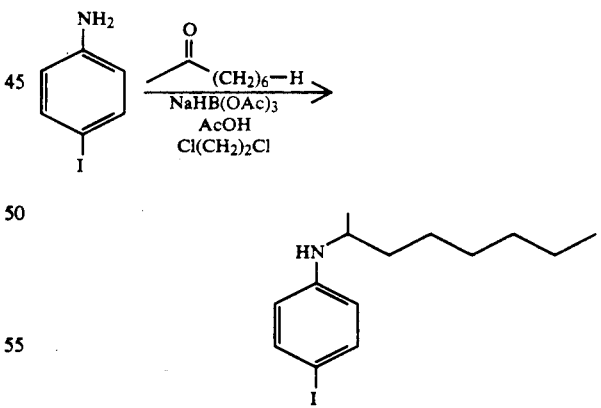

A flask containing 4-iodoaniline (11.0 g, 50.2 mmol) was charged with dry dichloroethane (125 ml), 2-octanone (7.9 ml, 50.0 mmol) and sodium triacetoxyborohydride (13.8 g, 65 mmol). After stirring for 10 minutes, acetic acid (2.9 ml, 50.7 mmol) was added via syringe over a 5 minute period. The reaction was stirred under an $N_2$ atmosphere for 16 hrs. At the end of this period the reaction was quenched by the careful addition of a solution of saturated aqueous ammonium chloride (100 ml). After stirring for 0.5 hr, the reaction was poured over ether (250 ml) and the layers were separated. The ether layer was washed with saturated aqueous ammonium chloride (100 ml), dried ($Na_2SO_4$), filtered and evaporated in vacuo. Flash column chromatography (silica, 1:39; EtOAC:hexanes) provided N-(4'-iodophenyl)-2-amino octane (14.6 g, 88%) as a light yellow oil.

Title Compound: $^1H$ (300 MHz) and $^{13}C$ (75 MHz) NMR spectra were consistent with the desired structure. Calculated for $C_{14}H_{22}NI$: C, 50.97; H, 6.69; I, 38.31. Found: C, 51.19, H, 6.72; I, 37.94.

Compositions of the Present Invention

The contrast agents may be formulated for administration using physiologically acceptable carriers or excipients in a manner within the skill of the art. The compounds with the addition of pharmaceutically acceptable aids (such as surfactants and emulsifiers) and excipients may be suspended or partially dissolved in an aqueous medium resulting in a dispersion, solution or suspension. However, the oily contrast agents are preferably made into emulsions.

Compositions of the present invention comprise the following pharmaceutically acceptable components based on % w/v:

| | |
|---|---|
| Non-aqueous phase | 1-50 |
| Contrast Agent | 0.001-75 |
| Excipient | 0-20 |
| Aids/Surfactants/Emulsifiers) | 0.01-15 |
| Water | q.s. to 100 |

Specific Examples of the compositions of the present invention are shown in Examples 3 and 4.

EXAMPLE NO. 3

| | |
|---|---|
| N-acetyl-N-2'-octyl-4-iodoaniline | 23.7% (w/v) |
| Safflower Oil | 20.0% (w/v) |
| Tween 21 | 2.5% (w/v) |
| Hydroxypropylmethylcellulose (4000 cPs) | 0.5% (w/v) |
| q.s with water to 100% volume and shake | |

EXAMPLE NO. 4

| | |
|---|---|
| N-(4'-iodophenyl)-2-amino octane | 55.3% (w/v) |
| Dow Corning Medical Antifoam AF | 40.0% (w/v) |
| q.s. with water to 100% volume and shake | |

The nonaqueous phase comprises vegetable oils such as safflower oil; non-metabolizing fat substituents, such as Simplesse; fluorinated hydrocarbons, such as perfluorodecalin; mineral oil and simethicone.

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl para-hydroxybenzoate, ethyl para-hydroxybenzoate, propyl para-hydroxybenzoate, benzoic acid or sorbic acid may also be desirable in some formulations.

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane (simethicone) and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 15% w/v of the aqueous formulations, although the amount, in general, is kept as low as possible, preferably in the range of 0.05 to 5% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

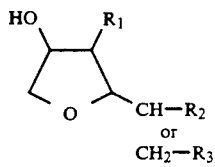

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=(C_{11}H_{23})$ COO for laurate, $(C_{17}H_{33})$ COO for oleate, $(C_{15}H_{31})$ COO for palmitate, $(C_{17}H_{35})$ COO for stearate.

Polyoxyethylene alkyl ethers (i.e. Brijs) having the formula:

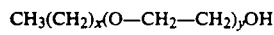

$CH_3(CH_2)_x(O-CH_2-CH_2)_yOH$ where $(x+1)$ is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60.

Polyethylene sorbitan fatty acid esters, sold under the trade names of Polysorbates 20, 40, 60, 65, 80 & 85.

Polyethylene stearates, such as:
poly(oxy-1,2-ethanediyl),α-hydro-ω-hydroxyoctadecanoate;
polyethylene glycol monostearate; and
poly(oxy-1,2-ethanediyl)-α-(1-oxooctadecyl)-ω-hydroxypolyethylene glycol monostearate The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular X-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% w/v and most preferably of from about 0.1% w/v to about 20% w/v.

The invention having been fully described, it will be apparent to one skilled in the art that changes and modifications can be made thereto without departing from the spirit and scope thereof.

What is claimed is:

1. An orally or rectally administerable x-ray contrast composition in a dispersion form for visualization of the gastrointestinal tract comprising a contrast agent having the formula, or a pharmaceutically acceptable salt thereof:

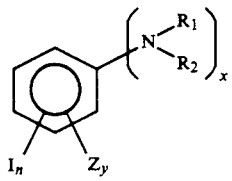

wherein
Z=H, halo, $C_1$-$C_{20}$ alkyl, cycloalkyl, lower alkoxy, cyano, where the alkyl and cycloalkyl groups can be substituted with halogen or halo-lower-alkyl groups;
$R_1$ and $R_2$ are independently H, $C_1$-$C_{25}$ alkyl, cycloalkyl, acetyl or halo-lower-alkyl, wherein said $C_1$-$C_{25}$ alkyl, cycloalkyl, and halo-lower-alkyl are optionally substituted with, fluoro-lower-alkyl, aryl, lower-alkoxy, hydroxy, carboxy, lower-alkoxy carbonyl or lower-alkoxy-carbonyloxy and said acetyl is optionally substituted with fluoro-lower-alkyl, aryl, lower alkoxy, hydroxy, lower-alkoxy carbonyl or lower-alkoxy-carbonyloxy;
n is 1–4;
y is 1–4; and
x is 1 or 2; and a physiologically acceptable carrier comprising a surfactant selected from the group consisting of cationic, anionic, nonionic, and zwitterionic surfactants.

2. The x-ray contrast composition of claim 1 wherein said contrast agent is selected from the group consisting of: N-acetyl-N-2'-octyl-4-iodoaniline and N-(4'-iodophenyl)-2-amino octane.

3. The x-ray contrast composition of claim 1 wherein said dispersion is an emulsion.

4. The x-ray contrast composition of claim 1 wherein said cationic surfactant is cetyl trimethylammonium bromide.

5. The x-ray contrast composition of claim 1 wherein said anionic surfactant is selected from the group consisting of sodium lauryl sulfate, sodium heptadecyl sulphate, an alkyl benzenesulphonic acid, sodium butylnaphthalene sulfonate and sulphosuccinate.

6. The x-ray contrast composition of claim 1 wherein said nonionic surfactant is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

7. The x-ray contrast composition of claim 1 further comprising a suspending agent.

8. The x-ray contrast composition of claim 1 further comprising a stabilizer.

9. The x-ray contrast composition of claim 1 further comprising an antioxidant.

10. The x-ray contrast composition of claim 1 further comprising an osmolality adjusting agent.

11. The x-ray contrast composition of claim 1 further comprising a buffering agent.

12. The x-ray contrast composition of claim 1 further comprising a pH adjusting agent.

13. The x-ray contrast composition of claim 1 further comprising a flavoring agent.

14. A method of carrying out x-ray examination of the gastrointestinal tract of a patient in need of such examination which comprises orally or rectally administering to the patient an x-ray contrast composition in a dispersion form comprising:

an x-ray contrast agent, or a pharmaceutically acceptable salt thereof, having the formula:

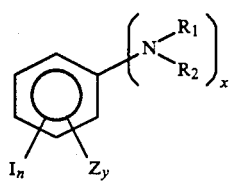

wherein

Z=H, halo, $C_1$-$C_{20}$ alkyl, cycloalkyl, lower alkoxy, cyano, where the alkyl and cycloalkyl groups can be substituted with halogen or halo-lower-alkyl groups;

$R_1$ and $R_2$ are independently H, $C_1$-$C_{25}$ alkyl, cycloalkyl, acetyl or halo-lower-alkyl, wherein said $C_1$-$C_{25}$5 alkyl, cycloalkyl, and halo-lower-alkyl are optionally substituted with halo, fluoro-lower-alkyl, aryl, lower-alkoxy, hydroxy, carboxy, lower-alkoxy carbonyl or lower-alkoxy-carbonyloxy and said acetyl is optionally substituted with fluoro-lower-alkyl, aryl, lower alkoxy, hydroxy, lower-alkoxy carbonyl or lower-alkoxy-carbonyloxy n is 1-4;

y is 1-4; and x is 1 or 2; and a physiologically acceptable carrier comprising a surfactant selected from the group consisting of cationic, anionic, nomonic, and zwitterionic surfactants.

15. The method of claim 14 wherein said contrast agent is selected from the group consisting of: N-acetyl-N-2'-octyl-4-iodoaniline and N-(4'-iodophenyl)-2-amino octane.

16. The method of claim 14 wherein the amount of contrast agent administered to said patient contains from about 0.1 to about 16 g iodine/kg body weight for regular x-ray visualization of the gastrointestinal tract.

17. The method of claim 14 wherein the amount of contrast agent administered to said patient contains from about 1 to about 600 mg iodine/kg body weight for CT scan visualization of the gastrointestinal tract.

18. The method of claim 14 wherein said contrast agent is in the form of an emulsion.

19. The method of claim 14 wherein said cationic surfactant is cetyl trimethylammonium bromide.

20. The method of claim 14 wherein said anionic surfactant is selected from the group consisting of sodium lauryl sulfate; sodium heptadecyl sulphate, an alkyl benzenesulphonic acid, sodium butylnaphthalene sulfonate and sulphosuccinates.

21. The method of claim 14 wherein said nonionic surface active agent is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

22. The method of claim 14 wherein said X-ray contrast composition further comprises a suspending agent.

23. The method of claim 14 wherein said X-ray contrast composition further comprises a stabilizer.

24. The method of claim 14 wherein said X-ray contrast composition further comprises an antioxidant.

25. The method of claim 14 wherein said X-ray contrast composition further comprises an osmolality adjusting agent.

26. The method of claim 14 wherein said X-ray contrast composition further comprises a buffering agent.

27. The method of claim 14 wherein said X-ray contrast composition further comprises a pH adjusting agent.

28. The method of claim 14 wherein said X-ray contrast composition further comprises a flavoring agent.

* * * * *